(12) United States Patent
Rebec

(10) Patent No.: US 8,180,422 B2
(45) Date of Patent: May 15, 2012

(54) NON-INVASIVE SYSTEM AND METHOD FOR MEASURING AN ANALYTE IN THE BODY

(75) Inventor: Mihailo V. Rebec, Bristol, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 1228 days.

(21) Appl. No.: 11/918,537

(22) PCT Filed: Apr. 13, 2006

(86) PCT No.: PCT/US2006/014152
§ 371 (c)(1),
(2), (4) Date: Oct. 15, 2007

(87) PCT Pub. No.: WO2006/113476
PCT Pub. Date: Oct. 26, 2006

(65) Prior Publication Data
US 2009/0062632 A1   Mar. 5, 2009

Related U.S. Application Data

(60) Provisional application No. 60/672,167, filed on Apr. 15, 2005.

(51) Int. Cl.
*A61B 5/1455* (2006.01)
(52) U.S. Cl. .................. 600/316; 600/322; 600/331
(58) Field of Classification Search .................. 600/310, 600/316, 322, 331, 335
See application file for complete search history.

(56) References Cited

U.S. PATENT DOCUMENTS

| | | | |
|---|---|---|---|
| 4,634,276 A | 1/1987 | Sharpe | |
| 4,645,340 A | 2/1987 | Graham et al. | |
| 4,975,581 A | 12/1990 | Robinson et al. | 250/339 |
| 5,039,855 A | 8/1991 | Kemeny et al. | 250/339 |
| 5,099,123 A | 3/1992 | Harjunmaa | |
| 5,120,961 A | 6/1992 | Levin et al. | 250/339 |

(Continued)

FOREIGN PATENT DOCUMENTS

EP   0 129 289 B1   9/1990

(Continued)

OTHER PUBLICATIONS

Malin et al., "Noninvasive Predicition of Glucose by Near-Infrared Diffuse Reflectance Spectroscopy," *Clinical Chemistry*, vol. 45, 1999, pp. 1651-1658.

(Continued)

*Primary Examiner* — Eric Winakur
*Assistant Examiner* — Chu Chuan (JJ) Liu
(74) *Attorney, Agent, or Firm* — Nixon Peabody LLP

(57) ABSTRACT

A system for determining an analyte concentration in a fluid sample (e.g., glucose) comprises a light source, a detector, and a central processing unit. The detector is adapted to receive spectral information corresponding to light returned from the fluid sample being analyzed and to convert the received spectral information into an electrical signal indicative of the received spectral information. The central processing unit is adapted to compare the electrical signal to an algorithm built upon correlation with the analyte in body fluid. The algorithm is adapted to convert the received spectral information into the analyte concentration in body fluid. Spectral information is delivered from the central processing unit to the light source and used to vary the intensity and timing of the light to improve the accuracy of conversion into analyte concentration.

19 Claims, 6 Drawing Sheets

U.S. PATENT DOCUMENTS

| | | | |
|---|---|---|---|
| 5,137,023 A | 8/1992 | Mendelson et al. | |
| 5,178,142 A | 1/1993 | Harjunmaa et al. | 600/310 |
| 5,179,951 A | 1/1993 | Knudson | 128/633 |
| 5,183,042 A | 2/1993 | Harjunmaa et al. | 128/633 |
| 5,309,907 A * | 5/1994 | Fang et al. | 600/342 |
| 5,348,003 A * | 9/1994 | Caro | 600/310 |
| 5,370,114 A | 12/1994 | Wong et al. | 128/633 |
| 5,372,135 A | 12/1994 | Mendelson et al. | |
| 5,435,309 A | 7/1995 | Thomas et al. | 128/633 |
| 5,477,321 A | 12/1995 | Johnson | 356/319 |
| 5,560,356 A | 10/1996 | Peyman | 128/633 |
| 5,606,164 A | 2/1997 | Price et al. | 250/339.09 |
| 5,615,673 A | 4/1997 | Berger et al. | |
| 5,636,633 A | 6/1997 | Messerschmidt et al. | 128/633 |
| 5,655,530 A | 8/1997 | Messerschmidt | 128/633 |
| 5,710,630 A | 1/1998 | Essenpreis et al. | |
| 5,750,994 A | 5/1998 | Schlager | 250/339.11 |
| 5,754,289 A | 5/1998 | Ozaki et al. | |
| 5,815,277 A | 9/1998 | Zare et al. | 356/440 |
| 5,823,951 A | 10/1998 | Messerschmidt | 600/322 |
| 5,830,132 A | 11/1998 | Robinson | 600/310 |
| 5,923,482 A | 7/1999 | Gilby | |
| 5,935,062 A | 8/1999 | Messerschmidt et al. | 600/322 |
| 5,978,691 A | 11/1999 | Mills | 600/334 |
| 6,044,285 A | 3/2000 | Chaiken et al. | |
| 6,064,897 A | 5/2000 | Lindberg et al. | 600/316 |
| 6,070,093 A | 5/2000 | Oosta et al. | 600/316 |
| 6,101,405 A | 8/2000 | Yasuda et al. | |
| 6,137,641 A | 10/2000 | Gilby | |
| 6,157,041 A | 12/2000 | Thomas et al. | 250/573 |
| 6,167,290 A | 12/2000 | Yang et al. | |
| 6,172,743 B1 | 1/2001 | Kley et al. | |
| 6,219,565 B1 | 4/2001 | Cupp et al. | 600/310 |
| 6,222,189 B1 | 4/2001 | Misner et al. | |
| 6,223,063 B1 | 4/2001 | Chaiken et al. | |
| 6,241,663 B1 | 6/2001 | Wu et al. | 600/310 |
| 6,278,889 B1 | 8/2001 | Robinson | 600/322 |
| 6,289,230 B1 | 9/2001 | Chaiken et al. | |
| 6,292,686 B1 | 9/2001 | Chaiken et al. | |
| 6,332,092 B1 | 12/2001 | Deckert et al. | |
| 6,352,502 B1 | 3/2002 | Chaiken et al. | |
| 6,370,406 B1 | 4/2002 | Wach et al. | 600/310 |
| 6,377,828 B1 | 4/2002 | Chaiken et al. | |
| 6,389,306 B1 | 5/2002 | Chaiken et al. | |
| 6,486,948 B1 | 11/2002 | Zeng | |
| 6,503,478 B2 | 1/2003 | Chaiken et al. | |
| 6,560,478 B1 | 5/2003 | Alfano et al. | |
| 6,574,490 B2 | 6/2003 | Abbink et al. | |
| 6,615,061 B1 | 9/2003 | Khalil et al. | |
| 6,636,305 B2 | 10/2003 | Zhao et al. | |
| 6,681,133 B2 | 1/2004 | Chaiken et al. | |
| 6,690,966 B1 | 2/2004 | Rava et al. | |
| 7,299,079 B2 | 11/2007 | Rebec et al. | |
| 7,308,293 B2 | 12/2007 | Gerlitz | 600/318 |
| 7,603,151 B2 | 10/2009 | Rebec et al. | |
| 2002/0016534 A1 | 2/2002 | Trepagnier et al. | 600/316 |
| 2003/0023170 A1 | 1/2003 | Gardner et al. | |
| 2003/0071993 A1 | 4/2003 | Zhao et al. | |
| 2003/0120137 A1 | 6/2003 | Pawluczyk | |
| 2004/0092804 A1 | 5/2004 | Rebec et al. | 600/310 |
| 2004/0152992 A1 | 8/2004 | Zeng | |
| 2005/0043597 A1 | 2/2005 | Xie | |
| 2008/0045820 A1 | 2/2008 | Rebec et al. | |
| 2008/0045821 A1 | 2/2008 | Rebec et al. | |
| 2010/0022860 A1 | 1/2010 | Rebec et al. | |

FOREIGN PATENT DOCUMENTS

| | | |
|---|---|---|
| EP | 0 636 232 B1 | 1/1998 |
| EP | 0 404 562 | 8/1998 |
| EP | 1 335 199 A1 | 8/2003 |
| GB | 2 328 279 | 2/1999 |
| JP | 2000/186998 | 7/2000 |
| JP | 2008/536580 | 9/2008 |
| TW | 200722051 | 6/2007 |
| WO | WO 99/59464 | 11/1999 |
| WO | WO 00/74753 | 12/2000 |
| WO | WO 02/084237 A1 | 10/2002 |
| WO | WO 03/023339 A1 | 3/2003 |
| WO | WO 03/056311 A1 | 7/2003 |
| WO | WO 2004/023125 A2 | 3/2004 |
| WO | WO 2004/064627 A1 | 8/2004 |
| WO | WO 2005/004712 | 1/2005 |
| WO | WO 2005/004712 A1 | 1/2005 |
| WO | WO 2006/113476 A2 | 10/2006 |
| WO | WO 2006/127766 A1 | 11/2006 |

OTHER PUBLICATIONS

Cameron et al., "The Use of Polarized Laser Light Through the Eye for Noninvasive Glucose Monitoring," *Diabetes Technology & Therapeutics*, vol. 1, No. 2, 1999, pp. 135-143.

Youcef-Toumi et al., "Noninvasive Blood Glucose Analysis Using Near Infrared Absorption Spectroscopy," *MIT Home Automation and Healthcare Consortium*, Progress Report No. 2-5: Mar. 31, 2000, pp. 1-7.

Z. Huang, H. Zeng, I. Hamzavi, D. McLean, and H. Lui, "Rapid Near-Infrared Raman Spectroscopy System for Real-Time In Vivo Skin Measurements", Optics Letters, 26 (22), 1782-1784 (2001).

Borchert, et al., "A Noninvasive Glucose Monitor: Preliminary Results in Rabbits", *Diabetes Technology & Therapeutics*, vol. 1, No. 2, 1999, Mary Ann Liebert, Inc. (pp. 145-151).

"Laser-Based Measurement of Glucose in the Ocular Aqueous Humor: An Efficacious Portal For Determination of Serum Glucose Levels" by Paul G. Steffes, Ph.D., *Diabetes Technology & Therapeutics*, vol. 1, No. 2, 1999, Mary Ann Liebert, Inc. (pp. 129-133).

Haaland et al., "Reagentless Near-Infrared Determination of Glucose in Whole Blood Using Multivariate Calibration," *Applied Spectroscopy*, vol. 46, No. 10, 1992, pp. 1575-1578.

Robinson et al., "Noninvasive Glucose Monitoring in Diabetic Patients: A Preliminary Evaluation," *Clinical Chemistry*, vol. 38, No. 9, 1992, pp. 1618-1622.

Marbach et al., "Noninvasive Blood Glucose Assay by Near-Infrared Diffuse Reflectance Spectroscopy of the Human Inner Lip," *Applied Spectroscopy*, vol. 47, No. 7, 1993, pp. 875-881.

Danzer et al., "Non-invasive Determination of Glucose by NIR Reflectance Measurements and Chemometric Evaluation," Source unknown, date unknown, 4 pgs.

Tran et al., "Electronic Tuning, Amplitude Modulation of Lasers by a Computer-Controlled Acousto-optic Tunable Filter," *Applied Spectroscopy*, vol. 46, No. 7, 1992, pp. 1092-1095.

Burmeister et al., "Evaluation of Measurement Sites for Noninvasive Blood Glucose Sensing with Near-Infrared Transmission Spectroscopy," *Clinical Chemistry*, vol. 45, 1999, pp. 1621-1627.

Mackenzie et al., "Advances in Photoacoustic Noninvasive Glucose Testing," *Clinical Chemistry*, vol. 45, 1999, pp. 1587-1595.

Malin et al., "Noninvasive Prediciton fo Glucose by Near-Infrared Diffuse Reflectance Spectroscopy," *Clinical Chemistry*, vol. 45, 1999, pp. 1651-1658.

Khalil, "Spectroscopic and Clinical Aspects of Noninvasive Glucose Measurements," *Clinical Chemistry*, vol. 45, No. 2, 1999, pp. 165-177.

Cameron et al., "The Use of Polarized Laser Light Through the Eye for Noninvasive Glucose Monitoring," *Diabetes Technology & Therapeutics*, vol. 1 , No. 2, 1999, pp. 135- 143.

Editorial; "Noninvasive Laser Measurement of Blood Glucose in the Eye: A Bright Idea or an Optical Illusion?," *Diabetes Technology & Therapeutics*, vol. 1, No. 2, 1999, pp. 117-119.

Ward et al., "Post-Prandial Blood Glucose Determination by Quantitative Mid-Infrared Spectroscopy," *Applied Spectroscopy*, vol. 46, No. 6, 1992, pp. 959-965.

Pan et al., "Near-Infrared Spectroscopic Measurement of Physiological Glucose Levels in Variable Matrices of Protein and Triglycerides," *Analytical Chemistry*, vol. 68, No. 7, Apr. 1, 1996, pp. 1124-1134.

Sowa et al., "Noninvasive Assessment of Regional and Temporal Variations in Tissue Oxygenation by Near-Infrared Spectroscopy and Imaging," *Applied Spectroscopy*, vol. 51, No. 2, 1997, pp. 143-152.

Müller et al., "Non-invasive blood glucose monitoring by means of near infrared spectroscopy: methods for improving the reliability of the calibration models," *The International Journal of Artificial Organs*, vol. 20, No. 5, 1997, pp. 285-290.

Borchert et al., "A Noninvasive Glucose Monitor: Preliminary Results in Rabbits," *Diabetes Technology & Therapeutics*, vol. 1, No. 2, 1999, pp. 145-151.

Youcef-Toumi et al., "Noninvasive Blood Glucose Analysis Using Near Infrared Absorption Spectroscopy," *MIT Home Automation and Healthcare Consortium*, Progress Report No. 2-5: Mar. 31, 2000, pp. 1-7.

Written Opinion of the International Searching Authority corresponding to the co-pending International Patent Application No. PCT/US2006/014152, European Patent Office, dated Nov. 28, 2006, 4pages.

International Search Report corresponding to co-pending International Patent Application No. PCT/US2006/014152, European Patent Office, dated Nov. 28, 2006, 8 pages.

* cited by examiner

NON-INVASIVE SYSTEM AND METHOD FOR MEASURING AN ANALYTE IN THE BODY

Cross-Reference to Related Applications

This application claims priority to Application No. 60/672,167 filed on Apr. 15, 2005, which is incorporated by reference in its entirety.

FIELD OF THE INVENTION

The present invention relates generally to systems for the determination of analytes by their interaction with infrared, visible, or ultraviolet radiation. In some important applications, analytes in body fluids are measured, (e.g., non-invasive measuring of glucose in the body).

BACKGROUND OF THE INVENTION

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. Their judgment may become impaired and they may eventually pass out. A person can also become very ill if their blood glucose level becomes too high—a condition known as hyperglycemia. Both conditions, hypoglycemia and hyperglycemia, are potentially life-threatening emergencies.

Common methods for monitoring a person's blood glucose level are invasive in nature. Typically, to check the blood glucose level, a drop of blood is obtained from the fingertip using a lancing device. The blood drop is produced on the fingertip and the blood is harvested using a test sensor which is inserted into a testing unit. The test sensor draws the blood to the inside of the test unit which then determines the concentration of glucose in the blood.

One problem associated with this type of analysis is that there is a certain amount of pain associated with the lancing of a finger tip. Diabetics must regularly self-test themselves several times per day. Each test requires a separate lancing, each of which involves an instance of pain for the user. Further, each lancing creates a laceration in the users skin which take time to heal and are susceptible to infection just like any other wound.

Other techniques for analyzing a person's blood glucose level are noninvasive in nature. Commonly, such techniques interpret the spectral information associated with light that has been transmitted through or reflected from a person's skin. An advantage of this type of noninvasive analysis is that there is no associated pain or laceration of the skin. However, thus far, such techniques have proven unreliable because many techniques fail to recognize the many issues that impact the analysis. For example, many noninvasive reflectance and transmission based systems do not account for the fact that the obtained spectral data contains glucose information from the portion of body tissue being analyzed as a whole, and is not limited to blood glucose. Other techniques do not account for irregularities in the spectral signal of the analyte due instrumental drift, temperature changes in the tissue under analysis, spectral characteristics of the tissue that change due to pressure changes, etc. that can occur during the analysis or between analyses. These irregularities can impact the quality of the calibration model or the algorithms that are used to determine the analyte concentrations from the noninvasively collected spectral data. The spectral data that has these irregularities cannot be used by the algorithms to determine the analyte concentrations.

Accordingly, there exists a need for a reliable noninvasive system for the determination of analytes in body fluids.

Near infrared radiation has been applied non-invasively in attempts to identify the glucose content of a patient's blood. However, non-invasive methods subject to the infrared radiation areas of the body that contain blood vessels, but other fluids containing glucose are present. A person's skin contains glucose in the extracellular fluid, which includes plasma and interstitial fluid. Since measurements of glucose by non-invasive methods are made in the dermis, they primarily determine the glucose in the extracellular fluid, plus some glucose in blood contained in capillaries in the skin. What is wanted is a correlation with the glucose content of blood, typically a small amount in the general range of 50 to 450 mg/dL. Now, it will be evident that if absorption of infrared radiation at specific wavelengths that are associated with glucose could be detected and measured, then the desired information will have been obtained. In practice, the presence of water and other materials that absorb infrared radiation make it difficult to measure the amount of glucose in the blood that is present and exposed to the infrared radiation. Some research has been directed to comparing the absorption of infrared radiation at certain wavelengths with a reference beam that has not been directed to the skin of a subject. More commonly, attempts have been made to correlate the response of a subject to a broadband of infrared radiation with measurements made by reliable methods of determining the glucose content of blood obtained by invasive methods.

In some patents including U.S. Pat. Nos. 5,435,309 and 5,830,132, methods are described in which, rather than applying a broadband of radiation or pre-selected wavelengths, a band of infrared radiation is scanned using acousto-optic tunable filters (AOTF). These solid state devices permit rapid scanning of a band of radiation without using filters or moving parts. The response of the subject to the radiation is detected and correlated using techniques familiar to those skilled in the art such as, for example, partial least squares (PLS) and principal component analysis (PCA).

In co-pending U.S. patent application Ser. No. 10/361,895 published as U.S. 2004/0092804A1, an improved method of measuring glucose non-invasively that employs AOTF was disclosed. In addition to an algorithm developed to correlate the spectral information with direct measurements of glucose in a subject's blood, the system employed several unique features that improved accuracy and consistency. Those features included a clamping device for assuring good contact with body tissue and which provided precise temperature and pressure control at the point of measurement. A unique attachment clamping device, including sapphire rods, termed an optoid by the inventors, were provided to direct radiation into the measurement region and transmit light leaving the region to the radiator detector. The device represented an advance in the art, but further improvement was sought by the present inventor.

It will be evident from the above discussion that obtaining accurate measurements of small amounts of glucose in blood by non-invasive methods is difficult since the concentration of glucose is small relative to other materials in the sample area and its response to infrared radiation occurs in regions in which other materials in higher concentrations also respond. At least two important problems are involved. First, much of the incident radiation is absorbed or scattered and the amount actually received by the detector is small. Thus, improving the signal-to-noise ratio is important. Second, water is present in large amounts relative to glucose and interferes with accurate measurement of glucose. This is especially a problem with instruments that employ a wide band of infrared radiation such as scanning and diode array instruments. As discussed above, instruments using AOTF scan a predetermined radiation band. This makes possible adjusting the power of the monochromatic light provided by the AOTF device so that the signal received at pre-selected wavelengths is maximized across the entire spectral region. Due to the different absorbency and scattering characteristics of the skin in the infrared region, the spectrum collected from the skin can have orders of magnitude differences in intensity. The limitations of most systems are that they are not able to maximize the information quality across such a divergent spectral region. Improvement of the signal-to-noise ration would be advantageous. Varying skin characteristics that affect scattering and absorbance of infrared radiation can be accounted for and then the signal-to-noise ratio could be improved. Another improvement in an AOTF device would provide feedback to adjust the power and the scanning time to provide the most accurate results. Further improvement could be obtained by programming the AOTF to change the amplitude of the radiation in specific regions of the spectrum that are obtained from an interaction with a known glucose concentration. The information so obtained would help to characterize the scattering, absorbance, and interference effects associated with a pure glucose sample.

The present inventor has found that an improved non-invasive glucose-measuring instrument can be made employing the above-described principles. Such an improved instrument will be described in detail below. Furthermore, the principles employed in the glucose-measuring instrument may be applied more generally to measuring analytes in may other instances.

SUMMARY OF THE INVENTION

In its more general aspects, the invention includes an instrument that supplies a source of infrared, visible, or ultraviolet light to a sample believed to contain an analyte and that retrieves returned light reflected from or transmitted through the sample and determines the amount of the analyte by the absorption of the light. The non-invasive system for measuring glucose in the fluid in body tissue is one example. The light source may be an AOTF spectrometer, laser diode array, a filtered broad band light source, or other sources that provide light in predetermined wavelength regions to a sample being inspected. A central processing unit will control the supply of light to the sample and its measurement upon its return to a detector. The central processing unit will provide one or more sets of light spectra to improve accuracy of the conversion of the received spectral information into concentration of the analyte in the sample. Light spectra may include one or more of the following, preferably in sequence.
   a source of light in which each wavelength segment has equal intensity over the wavelength range
   a source of light in which the intensity of each wavelength segment is adjusted to provide returned light having equal intensity throughout the wavelength range
   a source of light in which a sample is exposed to light of predetermined wavelengths for varying times
   a source of light in which a sample is exposed to light only at wavelengths determined to have the least signal-to-noise ratio.
   a source of light in which a sample is exposed to light at wavelengths determined to have a high signal-to-noise ratio, but at which significant information regarding the analyte is believed to be present.
   a source of light that contains information that corrects for changes in the analyte-related spectrum by the sample, light delivery and collection methods such as fibers or lenses, and the detector distortions.
   a source of light containing concentration-related spectra that correct for non-linear responses of the analyte.

The results obtained with those light spectra that are intended to emphasize certain regions of returned light may also be achieved by using a uniform intensity light source and processing the returning light.

In one embodiment, the invention includes a system for determining the concentration of an analyte in the fluids in body tissue (e.g., glucose in extracellular fluids) that comprises an infrared light source, a monochromatic device (e.g., an AOTF), a body tissue interface, a detector, and a central processing unit. The body tissue interface is adapted to contact body tissue and to deliver light from the monochromatic light source across a predetermined wavelength range to the contacted body tissue. The detector is adapted to receive spectral information corresponding to infrared light transmitted through or reflected from the portion of body tissue being analyzed and to convert the received spectral information into an electrical signal indicative of the received spectral information. The central processing unit is adapted to compare the electrical signal to an algorithm built upon correlation with the analyte in body fluid, the algorithm adapted to convert the received spectral information into the concentration of the analyte in body fluids.

In one embodiment of the invention, the light is modulated to correspond with a spectrum obtained by interaction of the light with a pure glucose sample.

BRIEF DESCRIPTION OF THE FIGURES

FIG. 4b is a cross-sectional view taken generally along line 4b-4b of FIG. 4a.

FIG. 5 is a plot of the absorbency of reflection light versus wavelength of the reflected light according to one embodiment of the reflected-based system illustrated in FIG. 4a.

DETAILED DESCRIPTION OF THE PREFERRED EMBODIMENTS

In the discussion that follows, application of the general principles of the invention will be discussed with particular reference to the non-invasive measurement of the glucose content of body fluids, a method of commercial importance. Similarly, application of the methods of the invention could be applied to analyzing other analytes in the body fluids, such as cholesterol, hemoglobin, creatinine, alcohol, bilirubin, albumin, total proteins, and globulins. However, it should be understood that the invention is not limited to that specific application, but it can be applied in many other situations where analytes are determined by their interaction with infrared, visible, or ultraviolet light. For example, measuring glucose or other sugar molecules in fermentation processes.

Determining the glucose content of blood is commonly used to monitor the need for medication or dietary changes in diabetic patients. Non-invasive methods of measuring glucose have been of interest, since they avoid the need for sampling blood. Thus, in one important embodiment, the invention has application in non-invasive methods for measuring glucose in body tissue and in which light is either passed through or reflected from body tissue.

Transmission-Based System

Figure 1:
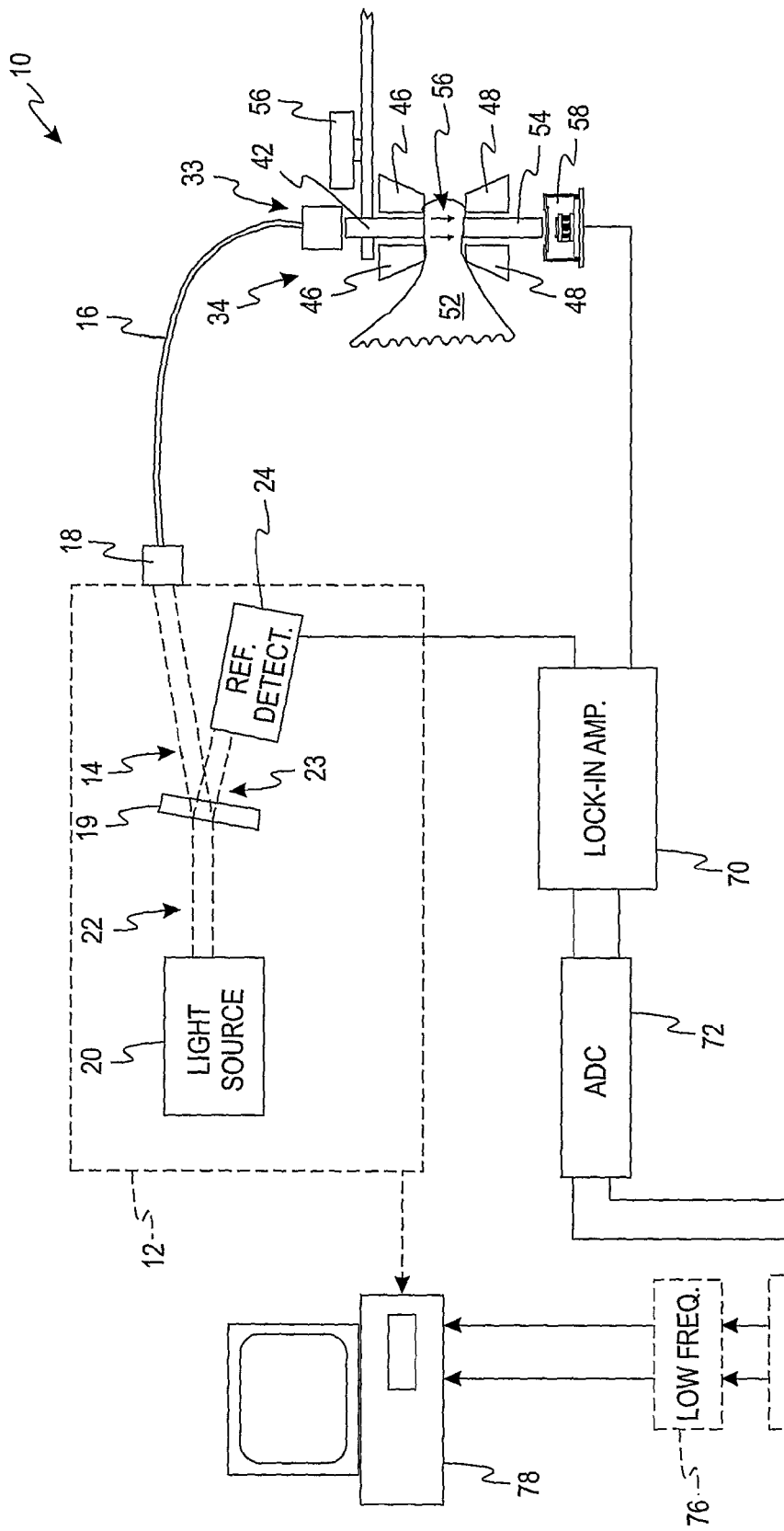
FIG. 1 is a diagram of a transmission-based system for determining analytes in body fluids.

Referring to FIG. 1, a transmission-based non-invasive system 10 for the determination of analytes in body fluids is functionally illustrated. The system 10 uses near infrared light transmitted through a piece of skin, such as the "web" of skin between a patient's index finger and thumb. Conventionally, a patient's glucose level measured in this way is referred to as their blood-glucose level. However, the measurement is principally made of glucose in the interstitial fluid and intercellular material. Accordingly, the present inventor prefers to refer to a patient's glucose level, which can be correlated with a patient's blood glucose level, as will be seen.

Human skin consists of approximately sixty percent extracellular material and 40% intracellular material. The extracellular material comprises approximately 30% plasma (blood) and about 70% interstitial fluid ("ISF"). Therefore, when examining the spectral characteristics of glucose from infrared light that is transmitted though a patient's skin, all the glucose in that portion of skin is being measured, rather than only the glucose in a patient's blood. The largest portion of the transmitted light is made up of light transmitted though ISF, and not blood plasma. Conversely, in an invasive setting where a 10 µl drop of blood is obtained on a patient's finger tip, for example, the measured glucose concentration primarily represents the concentration of glucose in that patient's blood, rather than in other fluids.

The system 10 is used to obtain transmitted spectral information from a patient for correlation with invasive measurements from the same patient. For example, the system 10 is used in a test wherein the glucose concentration of the test subject is modulated to a plurality of different concentration levels. One such test is a glucose clamping test where the glucose level of the test subject is raised and lowered to various levels over the duration of the test. According to one embodiment, the glucose clamping test is designed to bring the test subject's glucose level to six plateau regions that range in concentration from 50 to 300 mg/dL. Each plateau is separated by about 50 mg/dL so that each region can be clearly distinguished. ISF and plasma samples are collected throughout the duration of the clamping test. The samples are collected every five minutes and are analyzed for glucose content. This measurement is used to adjust the infusion of glucose or insulin to maintain the glucose concentration of the plasma for about twenty-five minutes at a particular targeted plateau region. The spectral data obtained over the course of the test are compared to the actual glucose levels (determined using invasive techniques) obtained during the test. From this data, a calibration algorithm is built to predict the actual glucose level of the patient based on the spectral characteristics of light transmitted through that patient's skin. This calibration algorithm can then be incorporated into a handheld version of the system 10 illustrated in FIG. 1.

Such a handheld instrument would enable a user to noninvasively monitor the user's glucose concentration level. The user would contact the user's skin with the instrument to obtain spectral information from the user's skin. The instrument would then provide the user with a reading of the user's glucose concentration level a short time later.

Sources of monochromatic infrared light include, for example, a Tungsten-Halogen light and an acoustic-optic tunable filter (AOTF). Referring to FIG. 1, an acoustic-optic tunable filter ("AOTF") spectrometer is shown generally by dashed line 12. The AOTF spectrometer 12 outputs a monochromatic, modulated beam of light 14 into a fiber optic cable 16 via a lens 18. The AOTF spectrometer 12 includes a light source 20. According to one embodiment, the light source 20 is a Tungsten-Halogen light source, which is a low-cost, stable light source that outputs a good amount of light (e.g., 250 watts). Alternative light sources include light emitting diodes ("LED"), doped fibers including uranium doped fibers, and laser diodes. The light source produces a beam of light 22 in the near-infrared region (i.e., having a wavelength ranging 750-2500 nanometers). This light is used to provide a series of monochromatic beams that scan across the beam width.

Generally, the AOTF spectrometer 12 functions as an electronically tunable spectral band-pass filter to output the monochromatic beam of light 14 having wavelengths within a desired range. The AOTF 12 is a solid state electro-optical device that consists of a crystal 19 in which acoustic (vibrational) waves, at radio frequencies ("RF") are used to separate a single wavelength of light from the broadband light source. The wavelength selection is a function of the frequency of the RF applied to the crystal 19. The crystal 19 used in AOTF devices can be made from a number of compounds. According to one embodiment of the present invention, the crystal comprises Tellurium Dioxide ($TeO_2$). $TeO_2$ crystals providing good results for use with light in the 1200 to 3000 nm spectral region. According to one embodiment, the crystal 19 is used in a non-collinear configuration, wherein the acoustic and optical waves (paths) through the crystal 19 are at very different angles from each other. Alternatively, collinear configured AOTF devices may be used. A transducer (not shown) is bonded to one side of the crystal. This transducer emits vibrations (acoustic waves) when RF is applied to the transducer.

As the acoustic waves pass from the transducer to the crystal 19, the crystal 19 alternately compresses and relaxes resulting in a refractive index variation that acts like a transmission diffraction grating. Unlike a classical grating, however, the crystal only diffracts one specific wavelength of light so it acts like a filter more than as a diffraction grating. The wavelength of the light that is diffracted is determined by a phase matching condition based on the birefringence of the $TeO_2$ crystal and the velocity and frequency of the acoustical wave and as well as parameters specific to the design of the AOTF. The wavelength that is selected is varied by simply changing the frequency of the applied RF. The diffracted light is directed into two first order beams that we call the positive and negative beams. The rest of the undiffracted light is passed through as undiffracted zero (0) order beam. The positive and negative beams are orthogonally polarized. The positive beam is delivered to the optoid as described below and the negative beam is used as a reference beam to correct for variations in the intensity of the light source or the efficiency of the AOTF as described below. Alternatively, the positive beam could be split and a portion used as a reference, while the remainder is sent to the optoid.

According to one embodiment, the beam of light 14 output by the AOTF spectrometer has a resolution or bandwidth of from about four to about ten nanometers ("nm"). This bandwidth is swept (back and forth) across a wavelength range of about 1400 to 2500 nanometers. Put another way, the AOTF spectrometer 12 outputs light having a wavelength continuously ranging between 1400 and 2500 nm and has a resolution of from about 4 to about 10 nm. The timing of the sweep can range from several milliseconds to several seconds. A suitable AOTF spectrometer is available from Crystal Technologies, Inc. of Palo Alto, Calif. as AOTF Model 2536-01. The AOTF spectrometer includes a RF driver, a mixer, and a low frequency oscillator (not shown) for modulating the monochromatic beam of light 14 at approximately 20,000 Hz. Although the light can be modulated at this frequency, others can be used to provide comparative results used to refine the corrections to the light spectra obtained.

A voltage control oscillator (not shown) provides the control of the RF frequency. Separate circuitry (not shown) is used for modulation and power control, which range from 0 to about 0.5 watts. A suitable voltage control oscillator is available from the Inrad Corporation, Northvale, N.J., Model DVCO-075A010. The power is delivered to an acoustical transducer that creates an acoustical wave that changes the characteristic of a birefringence crystal 19 so that full spectrum light is separated to wavelengths associated with a particular frequency and the rest of the light passes through as zero order light.

The crystal 19 of the AOTF spectrometer 12 splits the beam of light 22 into the first beam 14 and a second beam 23. The second beam of light 23 is directed to a reference detector 24 for measuring/recording the light input to the skin. Additionally, the reference detector 24 measures/records the light 23 for instrument drift associated with the light source and AOTF that can occur over time due to the length of operating time and change in temperature of the instrument over that time period.

The light 14 output by the AOTF spectrometer 12 is directed into the lens 18 that reduces the diameter of the beam of light and focuses the beam of light 14 into an end of the fiber optic cable 16. The lens 18 effectively couples the AOTF spectrometer 12 to the fiber optic cable 16. The fiber optic cable 16 is a low OH (i.e., preferably about 0.3 parts per million or below (of water in silica) fiber optic cable which has low attenuation over the length of the cable. The higher the OH content, the greater the intrinsic absorbance of the fiber itself especially in the wavelength region above 2100 nm. According to another embodiment, the fiber optic cable has an OH of less than about 0.12 ppm. The quality of light input to the fiber optic cable 16 is substantially maintained when delivered to a patient's skin at an opposite end 33 of the fiber optic cable 16. The output end 33 of the fiber optic cable 16 connects to a device the inventor has termed an optoid 34. Generally, the optoid 34 consists of the hardware that interfaces with the patient's skin. The optoid 34 includes a first plate 46 and a second plate 48, which are slideably clamped onto the tissue being analyzed, such as the web of skin 52 ("the web 52") of a patient's hand between the index finger and thumb. The optoid 34 includes a sapphire rod 42 that delivers light from the fiber optic cable 16 to the web 52. The sapphire rod 42, having a diameter of about three millimeters in one embodiment, increases the diameter of the beam of light input to the web 52. Fiber optic cables are typically limited in diameter to about two millimeters. The larger diameter of the sapphire rod 42 provides an effective means of coupling light that can be up to 3 mm in beam diameter to be delivered to the skin. Delivering a wider beam of light (e.g., the 3 mm of the sapphire rod as opposed to the 2 mm diameter of the fiber optic cable) covers a larger area of skin which limits the impact of small irregularities in skin properties. The sapphire rod 42 is flush with the interior surface of the first plate 46.

The light that is directed into the web 52 via the sapphire rod 42 is transmitted through the web 52 and into a second sapphire rod 54 (also 3 mm in diameter) disposed within the second plate 48. The light passing through the web 52 is generally represented by arrows 56. The amount of light transmitted through the web 52 is very low. Typically, less than about two percent of the light exiting the first sapphire rod 42 enters into the second sapphire rod 54. The light transmitted through the web 52 is directed by the second sapphire rod 54 into a detector 58. According to one embodiment of the present invention, the detector 58 is an extended Indium Gallium Arsenate ("InGaAs") detector having a circular active surface of three millimeters in diameter and provides a response across the 1300 to 2500 nm spectral region. Such a detector is commercially available from the Hamamatsu Corporation. According to one embodiment of the present invention, the reference detector 24 and the detector 58 are the same type of detector. Examples of other types of detectors that can be used in alternative embodiments of the present invention include Indium Arsenide ("InAs"), Indium Selenide ("InSe"), Lead Sulfide ("PbS"), Mercury-Cadmium-Telluride ("MCT"), and DTG detectors. Other types of detectors can be used depending on the desired region of the spectrum to be analyzed for determining the glucose concentration level. As is discussed in greater detail below in connection with FIG. 2, glucose exhibits unique spectral characteristics in the about 1450-1850 nm and the about 2200-2500 nm spectral range. The detector 58 generates an electrical signal indicative of the detected transmitted light, which is processed as is described in detail below.

In addition to providing a mechanism for transmitting light through the web 52, the optoid 34 performs other mechanical functions. First, the moveable first and second plates 46,48 (also referred to as "jaws") provide pressure to compress the web 52 to maintain a consistent optical path through the web 52. Compressing the web 52 brings a greater consistency to the testing process. According to one embodiment, the plates 46, 48 compress the tissue approximately six percent from its original thickness. Compressing the tissue also creates a flush interface between the web of skin and the plates 46,48 by eliminating air gaps between the web 52 and plates 46,48 so that the light transmitted from the first sapphire rod 42 directly enters the web 52. The optoid 34 includes a load cell 56 to measure the contact pressure on the web of skin 52. During the analysis, pressure measurements and temperature measurements are obtained so that irregularities associated with changes in pressure or temperature can be accounted for as discussed in greater detail below. Also, compressing the skin reduces the "noise" created by pulsing of the blood through the region being analyzed.

Second, each of the plates 46,48 includes thermal-electric heaters (not shown) that heat the web 52 to a uniform temperature. According to one embodiment of the present invention, the thermal-electric heaters heat the web to about 100° F.±0.1° F. The thermal-electric heaters, which are incorporated into each of the plates, are able to provide very accurate temperature control. Typically, the temperature differential between the surface of skin and the interior ranges between 5-7° F. Heating the skin to a substantially uniform level significantly reduces scattering of the light transmitted through the skin due to temperature gradients resulting in a more consistent analysis. Additionally, heating the skin to about 100° F. expands the capillaries and increases the amount of blood in the capillaries by approximately 300%, thus bringing more glucose into the area of analysis.

As discussed above, the AOTF 12 modulates the wavelength of the beam of light 14, which causes the beam of light transmitted through the skin via the optoid 34 to be modulated. The modulation aids in resolving some of the issues associated with instrument drift that can affect the quality of the spectral information. The modulated, transmitted light is received by the detector 58 and the modulated transmitted light strikes the active material of the detector 58 and is converted by the detector into an electrical current indicative of the light received. According to one embodiment, the electrical signal generated by the detector 58 is amplified by an amplifier (not shown) and sent to a lock-in amplifier 70, which demodulates the signal. A suitable lock-in amplifier 70 is available from Stanford Research Instruments, Model SR 810 DSP, according to one embodiment of the present invention. Alternatively still, the lock-in amplifier is integrated into an integrated circuit board comprising the described electrical hardware of the present invention.

An analog-to-digital converter 72 then digitizes the demodulated signal. According to one embodiment of the present invention, the analog-to-digital converter is a sixteen-bit converter available from National Instruments Corporation of Austin, Tex. It is contemplated that other analog-to-digital converters may be used. Alternatively, digitization is incorporated into an integrated circuit board comprising the described electrical hardware of the present invention. In other alternative embodiments, the digitization is at an 18 bit or higher bit rate.

The spectral data are optionally passed through a first filter 74 to remove high frequency noise and then a second filter 76 to remove slow drifting that occurs due to gradual changes in the patient's skin over the course of the analysis, or drift observed in the instrument or the optical fibers. Filtering the signal in this manner improves the overall signal-to-noise ratio.

The signal is then passed on to a central processing unit ("CPU") 78. The CPU 78 averages the received signal, resulting in approximately 500 data sets taken each minute over approximately 500 minutes. The data are saved with a tracking of the wavelength of the light input to the optoid 34. The spectral signal is also stored along with the time associated skin temperature, room temperature, pressure applied to the skin during the measurement, and blood pressure measurements. This information is useful in determining whether any irregularities in the spectral signal are the result of changes in these types of factors and not the result of changes in the glucose concentration. The data are then processed to improve the signal-to-noise quality of the data and to remove artifact effects that can corrupt the quality of the spectral data. According to alternative embodiments of the present invention, the processing to improve the signal-to-noise ratio can be accomplished in a variety of manners. For example, in one alternative embodiment, the signal-to-noise quality of the signal is improved by using Wavelet transforms to remove high frequency noise and low frequency baseline drift type of noise (i.e., irrelevant spectral variations that are determined by the information entropy corresponding to glucose levels). According to another alternative embodiment, the signal-to-noise quality is improved using such classical methods such as Savitsky-Golay multipoint smoothing. In other embodiments, first derivative analysis can be used to deal with baseline issues such as baseline drift type of noise.

Additionally, the noise in the signal is improved by removing spectral information that is not related to the relevant glucose information according to alternative embodiments of the present invention. This is accomplished by the application of a Genetic Algorithm for selecting wavelength regions that are the most related to the glucose changes and removing others that are not. This process results in the development of robust calibration algorithms that significantly reduce overfitting issues. In still another alternative embodiments, Orthogonal Signal Correction ("OSC") is employed to aid in the removal of non-glucose spectral information from the signal. This approach has proven beneficial in the removal of temperature and time drift related change imprints on the glucose-related data. Changes in the skin tissue result in changes in the scattering characteristics of the skin. Removing the data related to pressure and temperature changes over the course of the analysis results in a better calibration algorithm that results in better glucose predictions based on spectral data. Using a combination approach results in a more improved signal than using these different approaches individually. For example, the inventors have found that a combination of Wavelet processing and OSC has produced excellent results. Additionally, the inventors have found that the use of Genetic Algorithms in conjunction with OSC has produced excellent results.

Similarly, the reference detector 24 detects the beam of light 23, which is indicative of the light 14 provided to the optoid, and produces a "reference signal." The reference signal is processed in a manner similar to the signal produced by the detector 58.

Figure 2:
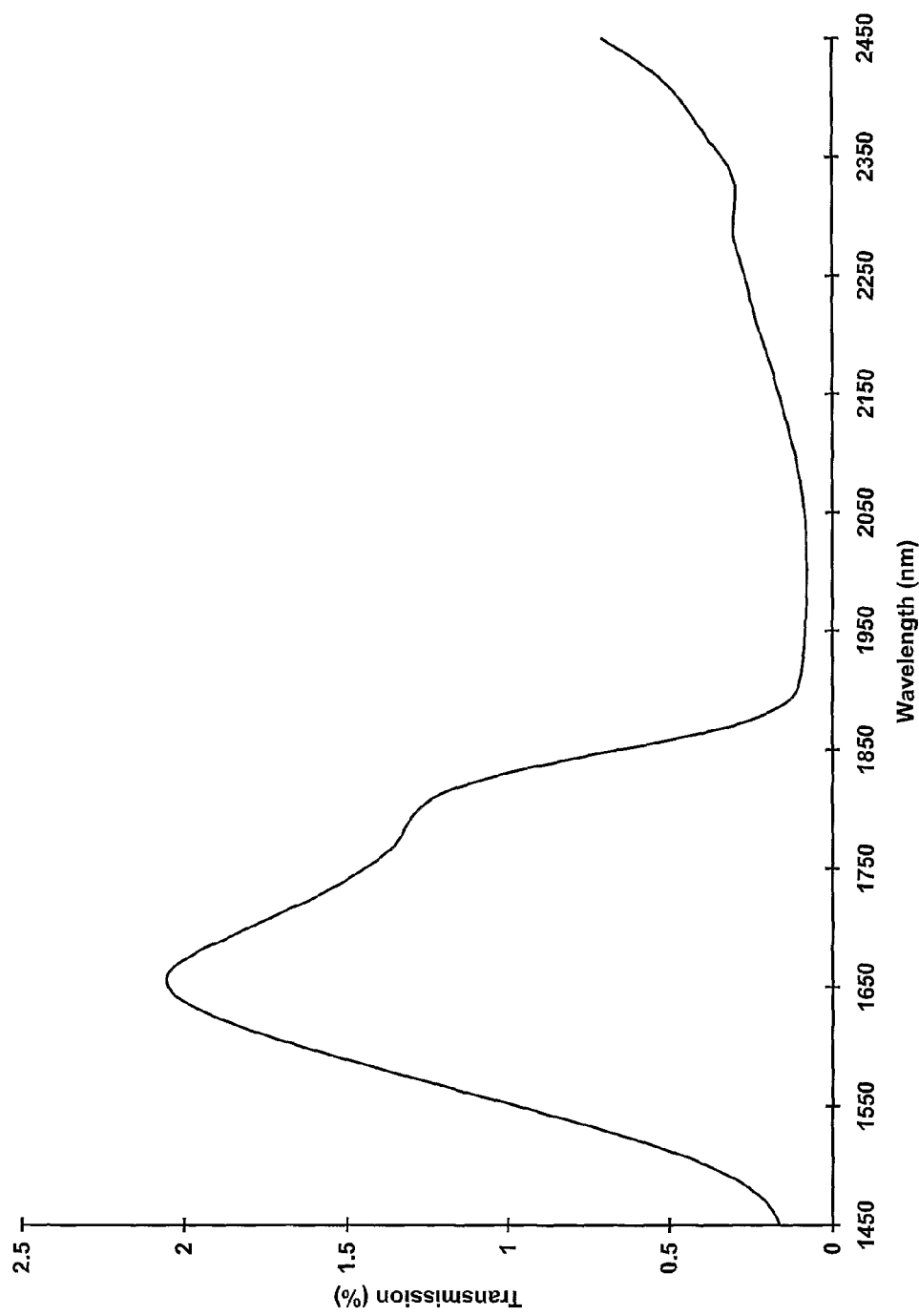
FIG. 2 is a plot of the absorbency of transmitted light versus wavelength of the transmitted light according to one embodiment of the transmission-based system illustrated in FIG. 1.

Referring now to FIG. 2, a plot of the percentage of light transmitted through the web versus wavelength (nm) is shown. The peaks in the plot between from about 1500-1850 nm and about 2100-2400 nm show a high transmission of light 56 though the tissue. The high absorbency outside these spectral ranges is due, in part, to absorption by the water contained in the skin. The glucose in the skin is present, in large part, where the water in the skin is located. Glucose exhibits unique spectral characteristics within these two wavelength ranges. More specifically, 1600-1730 nm and 2100-2380 nm regions.

The present invention provides further improvement of the signal-to-noise ratio of the signal-to-noise ratio of the signal received by the CPU. It will be recalled that the transmission of light varies as the wavelength of the light is varied by the AOTF (or other) source, as shown in FIG. 2. It has been found the large excursions above the base of the curve produce lower signal-to-noise ratios than would be desired. In some regions of the spectrum, the peaks are twenty times higher than in other parts of the spectrum. Thus, in one aspect the improved method of the invention the height of the peaks above the base line is effectively reduced in high transmission regions by reducing the intensity of the light in the appropriate wavelength region to reduce the height of the peak, with the result that the signal-to-noise ratio is improved by maximizing the dynamic range of the instrument in the spectral regions of interest. To accomplish this result, the CPU 78 is programmed to feed-back to the AOTF 12 (FIG. 1) the previously determined light transmitted at each wavelength and to reduce the intensity of the light in the region where peaks have been found.

Another improvement related to the feed-back of information to the AOTF is the modulation of the speed at which the wavelength range is scanned. Since valuable information is contained in the peaks of the transmission versus wavelength curve (e.g., FIG. 2). The scanning rate can be reduced within the peak regions to assure that the most accurate data is obtained. This also has been found to improve the signal-to-noise ratio, by averaging or integrating the data in such regions.

Further improvement can be obtained by programming the AOTF to change the amplitude of the radiation in specific regions of the spectrum determined by measuring the spectrum of a known composition, for example, a pure glucose sample or glucose in known fluids. The information obtained from such measurements would help to characterize the scattering, absorbance, and interference effects on the spectrum of glucose (or other analyte). The use of a glucose sample as a filter between the light source and the skin being tested may also be helpful in determining individual skin characteristics in sources where the glucose spectrum could not be programmed in, e.g. broadband light sources.

In combination, the two improvements just described have been shown to improve the signal-to-noise by a factor of 10, compared to the method in which the intensity of the examining light 14 is constant and the scanning rate is uniform.

As mentioned above, during the glucose clamping test, in addition to the transmitted spectral data, samples of blood and ISF are obtained from the test subject (e.g., the patient subjected to the test) to determine the subject's actual blood glucose level. According to one example of the glucose-clamping test, the test is conducted over an approximately 500 minute duration. The blood and ISF samples are obtained about every 5 minutes, totaling about 100 samples. These values are then interpolated over the 500 minute test duration, resulting in about 500 glucose concentration values.

The digital spectral signal of the transmitted light is averaged every minute and stored resulting in about 500 data sets over the course of the test duration. This data is then analyzed and processed (described in greater detail below) to build a calibration algorithm for predicting the actual glucose concentration level from an examination of the spectral characteristics of the transmitted light.

To obtain predicted values, it is necessary to build a calibration algorithm that predicts the glucose concentration from the transmitted spectral signal (i.e., the signal produced by the detector 58). After the spectral signal is filtered by the high and low frequency filters 74, 76, the signal is normalized to correct for changes in the spectral signal which are the results of spectral scattering of the light when transmitted through the web 52 and due to the pressure effects of the optoid 34 which is clamped to the web of skin 52. Failure to correct for these changes may obscure the spectral information associated with the glucose. As stated above, less than approximately two percent of the light input to the web of skin 52 is transmitted to the detector 58. Accordingly, it is important to account for these types of changes and irregularities that can lead to errors. The raw signal from the AOTF spectrometer described above is first normalized to constant energy, then mean centered to remove constant areas of the spectrum, creating a normalized, preprocessed series of spectra that are then checked for outliers by standard methods well known in the art. Further preprocessing by OSC reduction and wavelets analysis filtering are done to enhance the glucose signal and to suppress the water and other background signals. The resulting set of spectra is then used to build a calibration model by partial least squares (PLS) regression using Venetian blinds cross-validation on a portion of the data described above or on all of the data. Alternative embodiments to the data preparation described above involve other common methods for reduction or removal of background signal, including, but not limited to, first-derivative smoothing, second-derivative smoothing, wavelength selection by means of genetic algorithms, wavelet processing, and principal components analysis. Alternative embodiments for the generation of calibration models can be realized by many different forms of regression, including principal components regression, ridge regression or ordinary (inverse) least squares regression.

The calibration algorithm to predict the glucose concentration is then built from the normalized signal. An orthogonal signal correction process is combined with the time associated temperature and pressure information to identify the parts of the spectrum that are associated with these factors and not strictly related to the changes in the glucose concentration. This process is used in combination with the correlated data (i.e., the invasively determined glucose concentrations of the plasma and the ISF fluids) to filter out of the spectral data information that is associated with changes in the other measurements and not with changes in the glucose. This results in a calibration algorithm that is much more clearly associated with the changes in the glucose concentration, and less with artifacts that happen to correlate to the glucose concentration. Other data improvement processes include the use of more generic chemometric applications such as Genetic Algorithms and Wavelet analysis to further refine the spectral information to the most efficient information. The Genetic Algorithm and Wavelet analysis are able to select wavelengths in the spectrum that are specifically related to glucose and to permit the calibration algorithm to focus on specific changes in the glucose concentration. The selection is based on the area of the spectrum where the strongest glucose related peaks are located, but also the spectral areas related to the changes in the refractive index of the tissue due to changes in the tissue concentration. This wavelength selection process results in retaining the wavelength information that produces the best calibration algorithm.

Figure 3:
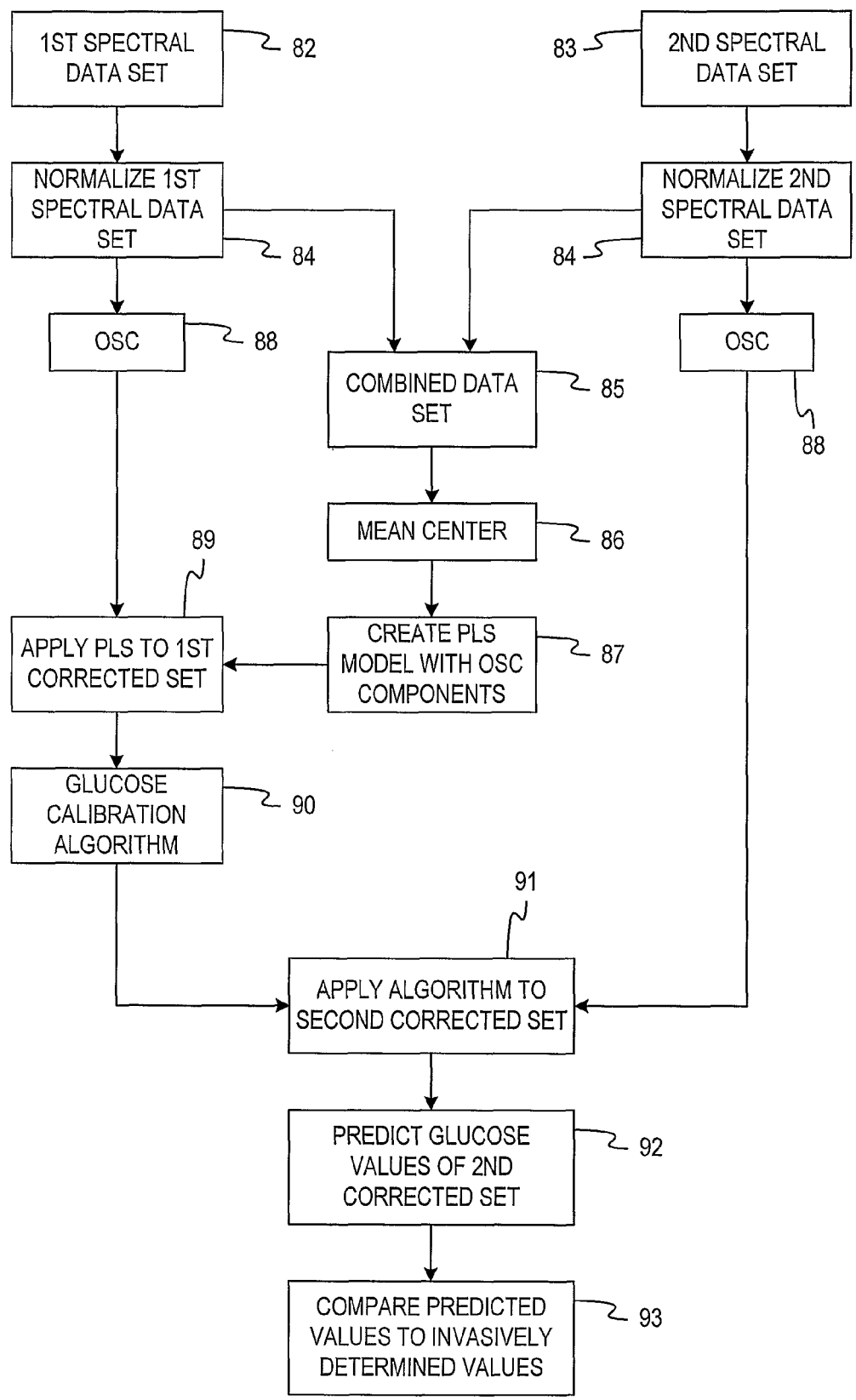
FIG. 3 is a flow chart depicting a method for building a glucose calibration algorithm.

Referring now to FIG. 3, a flow chart depicting a method of building the glucose calibration algorithm will be described according to one embodiment of the present invention. Initially, as described above, a glucose clamping experiment is conducted wherein spectral information is obtained from the body tissue of at least a first and a second test subject. This information is stored in a first data set 82 and a second data set 83. In one embodiment, each of the first and second data sets 82, 83 includes spectral information obtain from a plurality of test subjects. Other information such as body tissue temperature, pressure applied to the body tissue, and the invasively determined glucose concentration levels are obtained from each of the test subjects at predetermined intervals during the glucose clamping test.

A combined data set, consisting of spectral data from more than one test subjects (e.g., data from the first and second spectral data sets 82, 84), is prepared and used to generate a model useful for prediction of glucose levels for all of the subjects contributing data. The raw signals, stored in the first and second data sets 82, 84, from the AOTF spectrometer described above are first normalized at step 84 to constant energy for data from each of the test subjects. Portions of the data for each subject are then combined to form a single, combined spectral set at step 85, which is then mean centered at step 86 to remove constant areas of the spectrum, creating a normalized, preprocessed series of spectra that are then checked for outliers by standard methods known in the art. Further preprocessing by OSC reduction and wavelets analysis filtering are done to enhance the glucose signal and to suppress the water and other background signals. The resulting set of spectra is then used to build a calibration model by partial least squares (PLS) regression as step 87 using Venetian blinds cross-validation on a portion of the data described above or on all of the data. Alternative embodiments to the data preparation described above involve other common methods for reduction or removal of background signal, including, but not limited to, first-derivative smoothing, second-derivative smoothing, wavelength selection by means of genetic algorithms, wavelet processing and principal components analysis. Alternative embodiments for the generation of calibration models can be realized by many different forms of regression, including principal components regression, ridge regression or ordinary (inverse) least squares regression.

The PLS model, which was created at step 87, is applied to the orthogonal signal corrected, normalized first data set at step 89, which results in the glucose calibration algorithm at step 90. The glucose calibration algorithm 90 is used to predict glucose concentration based upon spectral information obtained from a test subject. Put another way, the glucose calibration algorithm is able to determine the glucose concentration of a test subject based upon the spectral information (e.g., transmitted or reflected spectral information) obtained from a test subject. The glucose calibration algorithm 90 is then applied to the orthogonal signal corrected, normalized second data set at step 91 for predicting the glucose contraction values of the test subject(s) of the second spectral data set 83 at step 92. The glucose concentration values predicted at step 92 are then compared to the invasively determined glucose concentration obtained during the glucose clamping test to check the accuracy of the glucose calibration algorithm at step 93.

In an alternative embodiment, building the glucose calibration algorithm also includes applying a Wavelets analysis to each of the data sets after OSC step 88, which filters the data. Additionally, in other alternative embodiments, the spectral data sets 82, 83 include spectral data modeled for glucose concentration levels which are outside the range of glucose concentration levels achieved during the glucose clamping test. In one embodiment, the AOTF spectrometer 12 can be used to create spectral data outside the ranges achieved during the glucose clamping test.

Reflectance-Based System

Figure 4A:
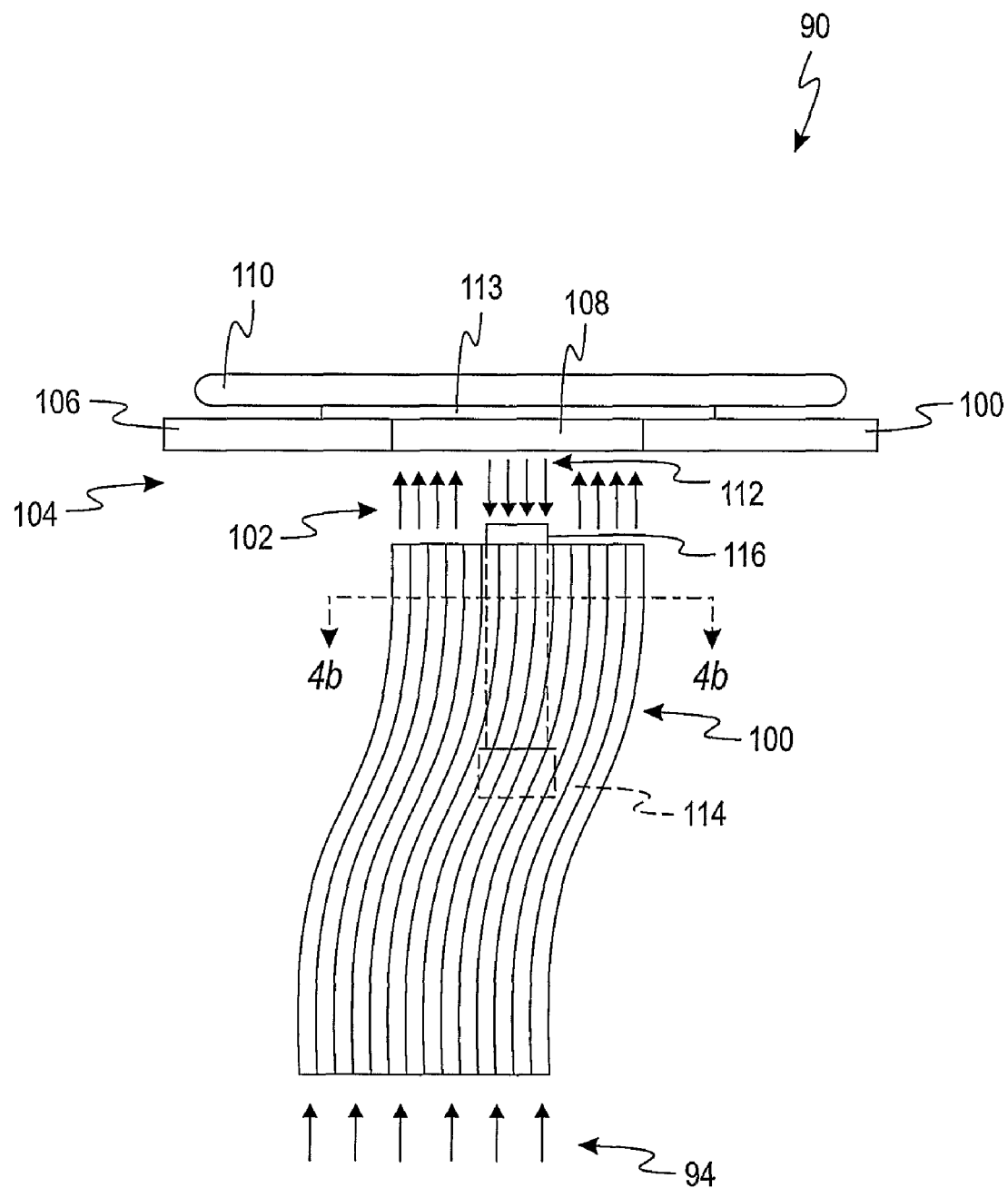
FIG. 4a is a diagram of the contact with the body of a reflectance-based system for determining analytes in body fluids.
Figure 4B:
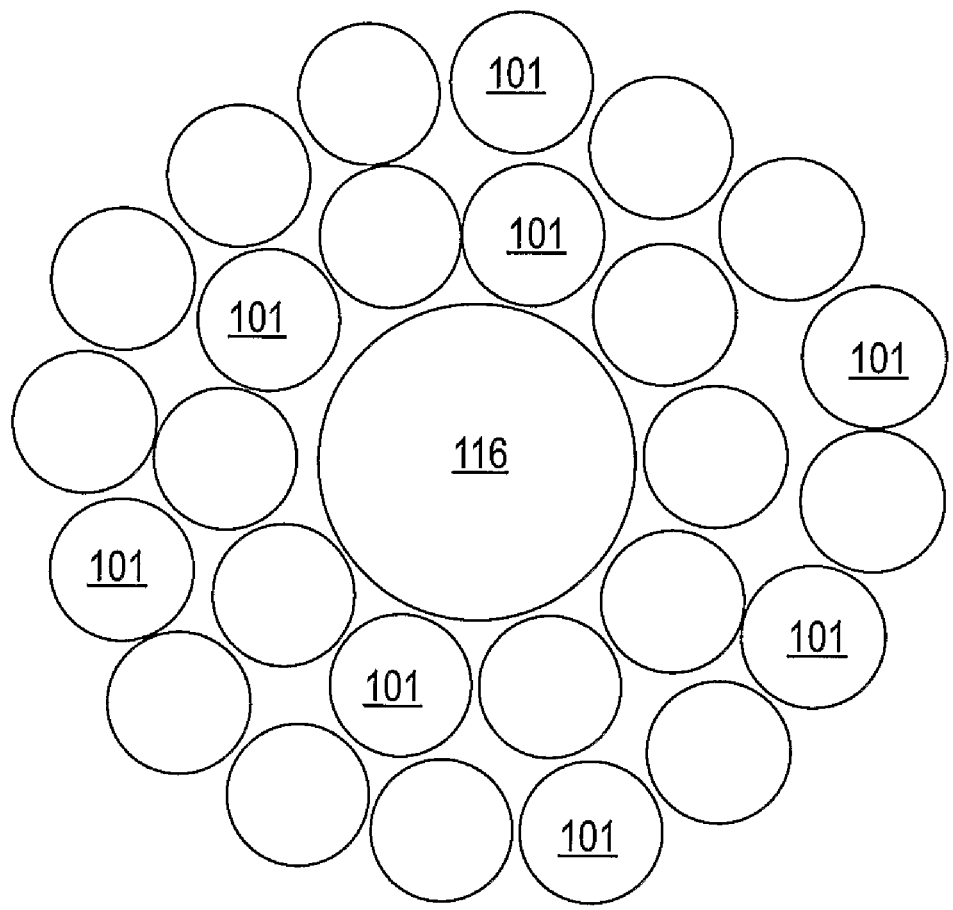

Referring now to FIGS. 4a and 4b, a reflectance-based non-invasive system 90 for the determination of analytes in body fluids is illustrated. Briefly, the system 90 inputs near infrared light into a portion of a patient's skin, such as a forearm, and records the amount of light reflected from the skin to determine the patient's glucose level.

A monochromatic beam of light is input to a bundle 100 of fiber optic cables. While the bundle 100 of fiber optic cables depicted in FIG. 5b shows two concentric circles or rows of fiber optic cables 101, any reasonable number of rows of fiber optic cable can be used. The monochromatic beam of light is generated in a manner similar to that described in connection with FIG. 1. An AOTF spectrometer (not shown) outputs a beam of light 94 having a resolution of four to ten nanometers ("nm"), which is swept (back and forth) across a wavelength range of about 2200-4500 nanometers to the fiber optic cable bundle 100. The fiber optic cable bundle 100 delivers light 94 to an optoid 104. The optoid 104 consists of the hardware that interfaces with a patient's skin. The optoid 104 includes a plate 106 having a window 108 formed therein. Light 102 is directed through the window 108 onto the patient's skin 110. According to one embodiment of the present invention, the window 108 is a sapphire window.

In use, the optoid 104 is brought into contact with a patient's skin 110 such as the patient's forearm, such that skin 110 rests on the plate 106 and window 108. Light 102 is directed through the window 108 into the skin 110. The light penetrates the skin 110 to a depth of about 300 microns and is then reflected from inside the skin 110. The reflected light 112 is represented by arrows. The reflected light 112 is directed to a detector 114 via a sapphire rod 116 disposed within the fiber optic bundle 100. The reflected light 112 is detected by the detector 114 in a manner similar to the transmitted light 56 discussed in connection with FIG. 1.

According to an alternative embodiment of the reflectance-based, non-invasive system 90, only a portion of the fiber optic cables 101 are used to deliver light to the optoid 104, which varies the path length of the delivered light. For example, only an inner ring of fiber optic cables 101 is utilized according to one embodiment and only the outer ring of fiber optic cables 101 are utilized according to another embodiment. Varying the path length of the delivered light allows the sampling of reflected light from different depths in the tissue. According to some embodiments, the various path lengths are used to correct for individual tissue characteristics such as scattering.

The optoid 104 of the reflectance-based non-invasive system 90 provides temperature control to the area of skin from which the reflectance signal is being taken. According to one embodiment of the present invention, the plates 106 of the optoid include thermoelectric heaters for heating the skin to approximately $100°\pm0.1°$ F. Again, heating the skin to uniform temperature reduces scattering of light, which is a function of temperature. Additionally, as discussed above, heating the skin causes the capillaries to expand thus increasing the volume of blood in the capillaries approximately three hundred percent.

According to one embodiment of the present invention, an index matching material 113 is disposed between the skin 110 and the window 108, for maintaining a constant and matched index for the light 102 directed into the skin 110 and the light reflected from the skin 112. The index matching gel reduces large index of refraction changes that would occur normally between skin and a gap of air. These large changes result in Fresnel losses that are especially significant in a reflectance based analysis, which creates significant changes in the spectral signal. According to one embodiment of the present invention, the indexing matching material is a chloro-fluoro-carbon gel. This type of indexing material has several favorable properties. First, the chloro-fluoro-carbon gel minimally impacts the spectral signal directed through the gel. Second, this indexing matching material has a high fluid temperature point so that it remains in a gel-like state during the analysis and under test conditions. Third, this gel exhibits hydrophobic properties so that it seals the sweat glands so that sweat does not fog-up (i.e., form a liquid vapor on) the sapphire window 108. And fourth, this type of index matching material will not be absorbed into the stratum corneum during the analysis.

The output of the detector 114 is filtered and processed in a manner similar to that described in conjunction with the above-described transmission-based system 10.

Figure 5:
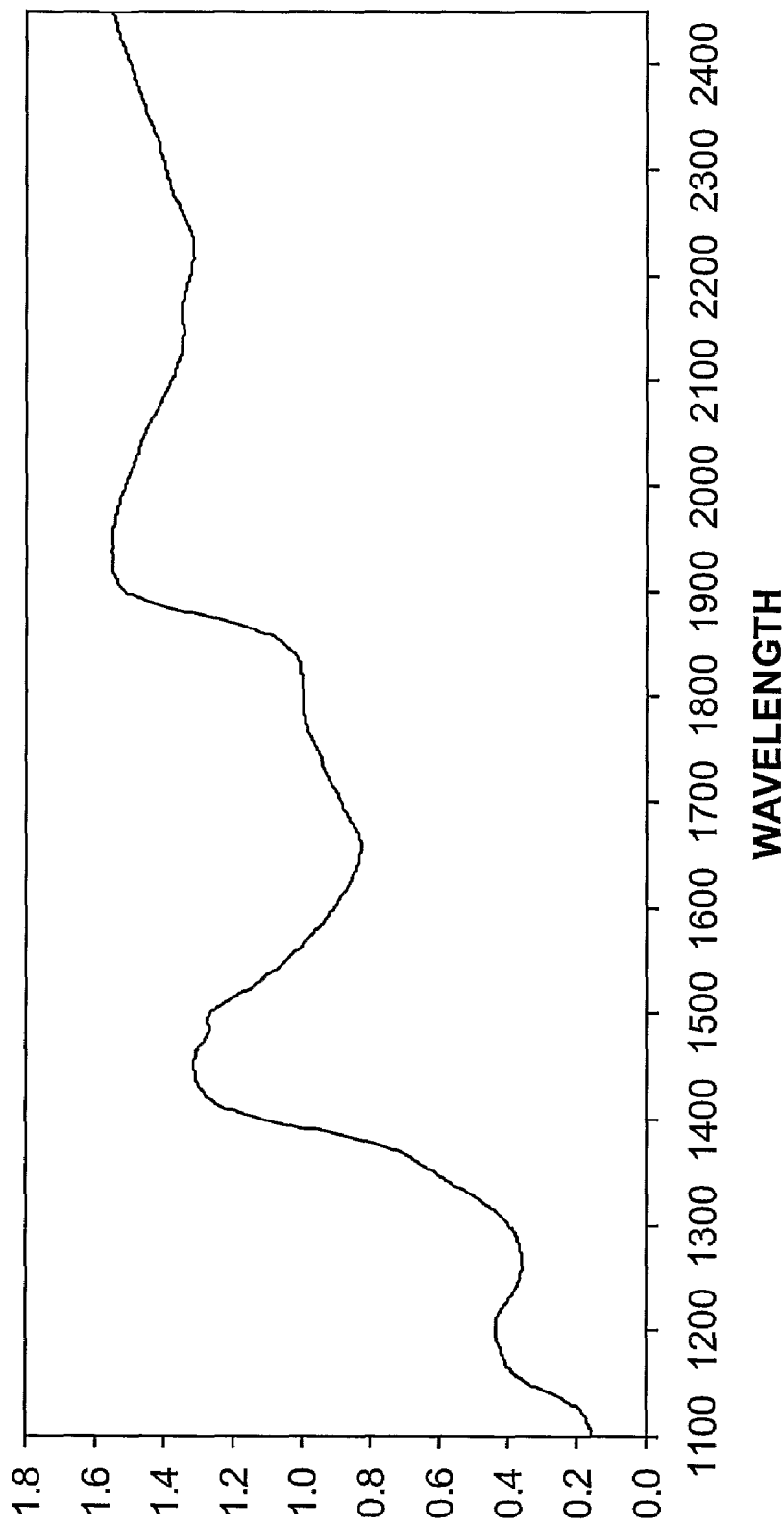

Referring now to FIG. 5, a plot of the absorption of light input to the skin versus wavelength is shown. As can be seen in FIG. 5, high absorption is observed in the 1350-1550 nm and the 1850-2050 spectral range.

The calibration algorithm for the reflectance-based system is built by applying similar data processing techniques as discussed in connection with the transmission-based system.

Varying the Applied Light or the Returning Light to Improve Accuracy

Once it has been seen how the invention may be employed in an important application, that is, the non-invasive determination of the glucose content of body fluid, the variations of the method may be more readily understood, including their applications where similar problems are found.

The proposed variations will be discussed first with reference to the measurement of glucose in the presence of substantial amounts of water, which interferes with the measurement of small amounts of glucose. The absorption of light by glucose and water affects the returning light, that is the reflected light or the transmitted light. Since the glucose and water have similar characteristics it is difficult to separate the absorption due to glucose from that of water. This is especially a problem when the analyte, glucose, is present in much smaller amounts relative to water. In the present invention, either the light source is manipulated by the central processing unit or the returning light is examined after detection in a related manner.

Consider the case in which an AOTF is used as a source of light. While it is easier to appreciate the variations of the method when they are applied to the use of an AOTF as the light source, it should be understood that other light sources may be used in instruments that measure analytes by means of their absorption of light within certain characteristic ranges. In the simplest case, the sample is exposed to light having a predetermined range of wavelengths. That range is swept through in sequence with equal intensity applied at each wavelength. Such a process produces the results shown in FIGS. 2 and 5. Since it is known that glucose (or another analyte) has certain characteristics, that is, it absorbs light at certain wavelengths more than others, the absorption of light does not clearly distinguish glucose in the presence of water without further manipulation of the data, as has been discussed earlier. The present invention also includes new processing steps that further improve the accuracy of the results, since the light absorbed is more easily characterized. The new processing steps are discussed as applied to altering the light produced by an AOTF, but may be applied similarly to processing of light returning from the sample to the detector.

Once the results of a scan of the suitable range of light wavelengths with uniform intensity is obtained, the central processing unit is programmed to repeat the scan, but with the intensity at each wavelength adjusted during the repeat scan so that the returning light has equal intensity at each of the wavelengths examined. Such a procedure has the effect of suppressing the relative absorption of water so that the signal-to-noise ratio is improved, because the detector becomes more sensitive to the presence of glucose at its characteristic wavelengths.

A further improvement may be obtained by scanning the desired range of wavelengths non-uniformly, that is, dwelling for longer periods at wavelengths identified as containing more useful information about the glucose, relative to water or to other interfering substances. Then, the returning light can be given more importance in the mathematical analysis of the data.

Another variation of the scanning process examines only those wavelengths where it has been found that the signal-to-noise ratio is the highest, that is, where the interference of water and other substances is the least. The effect of absorption by glucose would be likely to be more clearly seen and therefore the accuracy of the results would be expected to be improved.

A related method would examine only certain regions in which it has been found that information on glucose is more readily distinguished from water or other interfering substances. For example, the absorption of light by glucose and water broadly speaking occurs in similar regions. However, the response varies with temperature and it is therefore feasible to distinguish between glucose and water in certain regions where their difference in absorption of light is more easily seen as the temperature of the sample is varied.

The light source may also be supplied with information that corrects for changes in the analyte-related spectrum caused by the sample, the delivery and collection methods (e.g., fibers or lenses) and detector distortions. If changes to the returning light related to the associated equipment and the sample itself can be corrected for, determining the amount of the analyte can be done with improved accuracy.

For various reasons, the response of the analyte may not be as linear as would be expected. Therefore, the light source may contain concentration-related spectra that correct for the non-linearly of response.

It will be evident to those skilled in the art that some of the methods just discussed may be applied to the detection and analysis of data contained in light returning from the sample. Furthermore, any one or up to all of the improved methods may be applied in order to improve the signal related to the analyte and thus to increase the accuracy of the analysis. Preferably, a sequence of these methods would be applied to refine the determination of the analyte to improve the accuracy of the results.

While the present invention has been described with reference to one or more particular embodiments, those skilled in the art will recognize that many changes may be made thereto. Each of these embodiments and obvious variations thereof is contemplated as falling within the scope of the invention.

Alternative Embodiment A

A system for determining the concentration of an analyte in a fluid sample, the system comprising:

a light source delivering light within a predetermined wavelength range;

a detector adapted to receive spectral information corresponding to light returned from said fluid and to convert the received spectral information into an electrical signal indicative of the received spectral information; and a central processing unit adapted to compare the electrical signal to an algorithm built upon correlation with the analyte in the body fluid, the algorithm adapted to convert the received spectral information into the concentration of said analyte in said fluid, the central processing unit controlling the light source and varying the intensity and timing of the delivery of said light within said predetermined wavelength range to improve the accuracy of conversion of the received spectral information into concentration of said analyte in said fluid.

Alternative Embodiment B

The system of Alternative Embodiment A wherein said light source is a series of beams of monochromatic light that scan across the predetermined wavelength range.

Alternative Embodiment C

The system of Alternative Embodiment B further comprising a reference detector adapted to receive a portion of said series of beams of monochromatic light and to convert the received light into a reference electrical signal.

Alternative Embodiment D

The system of Alternative Embodiment C wherein said light source is adapted to modulate the monochromatic beams of light, and further comprising at least one lock-in amplifier electrically for demodulating the reference electrical signal and for demodulating the electrical signal indicative of the received spectral information.

Alternative Embodiment E

The system of Alternative Embodiment B wherein said monochromatic light is delivered to said fluid sample sequentially across a predetermined wavelength range.

Alternative Embodiment F

The system of Alternative Embodiment E wherein the intensity of said monochromatic light is uniform over said predetermined wavelength range.

Alternative Embodiment G

The system of Alternative Embodiment E wherein the intensity of said monochromatic light is varied across said predetermined wavelength range to provide spectral information received from said sample having uniform intensity across said predetermined wavelength range.

Alternative Embodiment H

The system of Alternative Embodiment E wherein said monochromatic light is delivered to said sample for predetermined periods of time at predetermined wavelengths.

Alternative Embodiment I

The system of Alternative Embodiment H wherein said monochromatic light is delivered to said sample at predetermined wavelengths where the signal-to-noise ratio is the greatest.

Alternative Embodiment J

The system of Alternative Embodiment H wherein said monochromatic light is delivered to said sample at predetermined wavelengths where said analyte is more readily distinguished from interfering substances.

Alternative Embodiment L

The system of Alternative Embodiment A wherein said light source delivers to said sample predetermined wavelengths of light at predetermined intensities and said spectral information returned from said sample is processed to provide spectral information having uniform intensity at said predetermined wavelengths.

Alternative Embodiment L

The system of Alternative Embodiment A wherein said light source delivers to said sample predetermined wavelengths of light at predetermined intensities and said spectral information returned from said sample is processed to provide spectral information at predetermined wavelengths where the signal-to-noise ratio is the greatest.

Alternative Embodiment M

The system of Alternative Embodiment A wherein said light source delivers to said sample predetermined wavelengths of light at predetermined intensities and said spectral information returned from said sample is processed to provide spectral information at wavelengths where said analyte is more readily distinguished from interfering substances.

Alternative Embodiment N

The system of Alternative Embodiment A wherein said light source contains information that is used to correct for the effect on the light spectra of the sample, light delivery and collection systems, and detector.

Alternative Embodiment 0

The system of Alternative Embodiment A wherein said light source contains information that corrects for changes in the analyte-related spectrum by the sample, light delivery and collection methods, and detector distortions.

Alternative Embodiment P

The system of Alternative Embodiment A wherein said light source contains concentration-related spectra that correct for non-linear responses of the analyte.

Alternative Process O

The method for determining the concentration of an analyte in a fluid sample, the method comprising the acts of:

delivering light within a predetermined wavelength range from a light source;

receiving spectral information corresponding to light returned from said fluid;

converting the received spectral information into an electrical signal indicative of the received spectral information;

comparing the electrical signal to an algorithm built upon correlation with the analyte in the body fluid; and converting the received spectral information into the concentration of said analyte in said fluid via a central processing unit, wherein the central processing unit controls the light source and varies the intensity and timing of the delivery of said light within said predetermined wavelength range to improve the accuracy of conversion of the received spectral information into concentration of said analyte in said fluid.

Alternative Embodiment R

A system for determining the concentration of an analyte in body tissue fluid, the system comprising:

an infrared light source delivering substantially monochromatic light sequentially across a predetermined wavelength range;

a body tissue interface adapted to contact body tissue and to deliver light from said infrared light source to the contacted body tissue;

a detector adapted to receive spectral information corresponding to infrared light transmitted through the contacted body tissue and to convert the received spectral information into an electrical signal indicative of the received spectral information; and a central processing unit adapted to compare the electrical signal to an algorithm built upon correlation with the analyte in the body fluid, the algorithm adapted to convert the received spectral information into the concentration of the analyte in the body fluid, said central processing unit controlling said infrared light source and varying the intensity and timing of the delivery of said monochromatic light within the predetermined wavelength range to improve the accuracy of conversion of the received spectral information into concentration of said analyte in said fluid.

Alternative Embodiment S

The system of Alternative Embodiment R wherein said infrared light source is an acoustic optical tunable filter (AOTF).

Alternative Embodiment T

The system of Alternative Embodiment S wherein said wavelength range is from about 1400 nanometers to about 2500 nanometers.

Alternative Embodiment U

The system of Alternative Embodiment R wherein said body fluid is extracellular fluid and said analyte is glucose.

Alternative Embodiment V

The system of Alternative Embodiment U wherein said infrared light source is modulated to correspond to a spectrum obtained by interaction of the infrared light with a pure glucose sample.

Alternative Embodiment W

The system of Alternative Embodiment U wherein the intensity of said monochromatic light is uniform over said predetermined wavelength range.

Alternative Embodiment X

The system of Alternative Embodiment U wherein the intensity of said monochromatic light is varied across said predetermined wavelength range to provide spectral information received from said sample having uniform intensity across said predetermined wavelength range.

Alternative Embodiment Y

The system of Alternative Embodiment U wherein said monochromatic light is delivered to said sample for predetermined periods of time at predetermined wavelengths.

Alternative Embodiment Z

The system of Alternative Embodiment Y wherein said monochromatic light is delivered to said sample at predetermined wavelengths where the signal-to-noise ratio is the greatest.

Alternative Embodiment AA

The system of Alternative Embodiment Y wherein said monochromatic light is delivered to said sample at predetermined wavelengths where said analyte is more readily distinguished from interfering substances.

Alternative Embodiment BB

The system of Alternative Embodiment U wherein said monochromatic light delivers to said sample predetermined wavelengths of light at predetermined intensities and spectral information returned from said sample is processed to provide spectral information having uniform intensity at said predetermined wavelengths.

Alternative Embodiment CC

The system of Alternative Embodiment U wherein said monochromatic light delivers to said sample predetermined wavelengths of light at predetermined intensities and said spectral information returned from said sample is processed to provide spectral information at predetermined wavelengths where the signal-to-noise ratio is the greatest.

Alternative Embodiment DD

The system of Alternative Embodiment U wherein said monochromatic light delivers to said sample predetermined wavelengths of light at predetermined intensities and said spectral information returned from said sample is processed to provide spectral information at wavelengths where said analyte is more readily distinguished from interfering substances.

Alternative Embodiment EE

The system of Alternative Embodiment U wherein said monochromatic light contains information that is used to correct for the effect on the light spectra of the sample, light delivery and collections systems, and detector.

Alternative Embodiment FF

The system of Alternative Embodiment U wherein said light source contains information that corrects for changes in the analyte-related spectrum by the sample, light delivery and collection methods, and detector distortions.

Alternative Embodiment GG

The system of Alternative Embodiment U wherein said light source contains concentration-related spectra that correct for non-linear responses of the analyte.

Alternative Process HH

A method for determining the concentration of an analyte in body tissue fluid, the method comprising the acts of:

delivering substantially monochromatic light from an infrared light source sequentially across a predetermined wavelength range;

contacting body tissue with a body tissue interface;

delivering light from said infrared light source to the contacted body tissue;

receiving spectral information corresponding to infrared light transmitted through the contacted body tissue;

converting the received spectral information into an electrical signal indicative of the received spectral information;

comparing the electrical signal to an algorithm built upon correlation with the analyte in the body fluid using a central processing unit; and converting the received spectral information into the concentration of the analyte in the body tissue fluid using the algorithm, wherein the central processing unit controls said infrared light source and varies the intensity and timing of the delivery of said monochromatic light within the predetermined wavelength range to improve the accuracy of conversion of the received spectral information into concentration of said analyte in said fluid.

Alternative Embodiment II

A system for determining the concentration of an analyte in body tissue fluid, the system comprising:

an infrared light source delivering substantially monochromatic light sequentially across a predetermined wavelength range;

a body tissue interface adapted to contact body tissue and to deliver light from said infrared light source to the contacted body tissue;

an index matching medium disposed between the body tissue interface and said body tissue, wherein the infrared light delivered to said body tissue and reflected by the body tissue passes through said index matching medium;

a detector adapted to receive light reflected from the body fluid and to convert the received reflected light into an electrical signal indicative of the received reflected light; and a central processing unit adapted to compare the electrical signal to an algorithm built upon correlation with the analyte in the body fluids, the algorithm converting the received spectral information into the concentration of the analyte in said body fluid, said central processing unit controlling said infrared light source and varying the intensity and timing of the delivery of said monochromatic light with the predetermined wavelength range to improve the accuracy of conversion of the received spectral information into concentration of said analyte in said fluid.

Alternative Embodiment JJ

The system of Alternative Embodiment II wherein said infrared light sources is an optical tunable filter (AOTF).

Alternative Embodiment KK

The system of Alternative Embodiment JJ wherein the infrared light has a wavelength ranging between approximately 1400 nanometers and approximately 2500 nanometers.

Alternative Embodiment LL

The system of Alternative Embodiment II wherein said body fluid is extracellular fluid and said analyte is glucose.

Alternative Embodiment MM

The system of Alternative Embodiment LL wherein said monochromatic infrared light is modulated to correspond to a spectrum obtained by interaction of the light with a pure glucose sample.

Alternative Embodiment NN

The system of Alternative Embodiment LL wherein the intensity of said monochromatic light is uniform over said predetermined wavelength range.

Alternative Embodiment OO

The system of Alternative Embodiment LL wherein the intensity of said monochromatic light is varied across said predetermined wavelength range to provide spectral information received from said sample having uniform intensity across said predetermined wavelength range.

Alternative Embodiment PP

The system of Alternative Embodiment LL wherein said monochromatic light is delivered to said sample for predetermined periods of time at predetermined wavelengths.

Alternative Embodiment QQ

The system of Alternative Embodiment PP wherein said monochromatic light is delivered to said sample at predetermined wavelengths where the signal-to-noise ratio is the greatest.

Alternative Embodiment RR

The system of Alternative Embodiment PP wherein said monochromatic light is delivered to said sample at predetermined wavelengths where said analyte is more readily distinguished from interfering substances.

Alternative Embodiment SS

The system of Alternative Embodiment LL wherein said monochromatic light delivers to said sample predetermined wavelengths of light at predetermined intensities and spectral information returned from said sample is processed to provide spectral information having uniform intensity at said predetermined wavelengths.

Alternative Embodiment TT

The system of Alternative Embodiment LL wherein said monochromatic light delivers to said sample predetermined wavelengths of light at predetermined intensities and said spectral information returned from said sample is processed to provide spectral information at predetermined wavelengths where the signal-to-noise ratio is the greatest.

Alternative Embodiment UU

The system of Alternative Embodiment LL wherein said monochromatic light delivers to said sample predetermined wavelengths of light at predetermined intensities and said spectral information returned from said sample is processed to provide spectral information at wavelengths where said analyte is more readily distinguished from interfering substances.

Alternative Embodiment VV

The system of Alternative Embodiment LL wherein said monochromatic light contains information that is used to correct for the effect on the light spectra of the sample, light delivery and collections systems and detector distortions.

Alternative Embodiment WW

The system of Alternative Embodiment LL wherein said light source contains information that corrects for changes in the analyte-related spectrum by the sample, light delivery and collection methods, and detector distortions.

Alternative Embodiment XX

The system of Alternative Embodiment LL wherein said light source contains concentration-related spectra that correct for non-linear responses of the analyte.

Alternative Process YY

A method for determining the concentration of an analyte in body tissue fluid, the method comprising the acts of:
  delivering substantially monochromatic light using an infrared light source sequentially across a predetermined wavelength range;
  contacting body tissue using a body tissue interface;
  delivering light from said infrared light source to the contacted body tissue;
  placing an index matching medium between the body tissue interface and said body tissue, wherein the infrared light delivered to said body tissue and reflected by the body tissue passes through said index matching medium;
  receiving light reflected from the body fluid;
  converting the received reflected light into an electrical signal indicative of the received reflected light;
  comparing the electrical signal to an algorithm built upon correlation with the analyte in the body fluids via a central processing unit; and
  converting the received spectral information into the concentration of the analyte in said body fluid,
  wherein the central processing unit controls said infrared light source and varies the intensity and timing of the delivery of said monochromatic light with the predetermined wavelength range to improve the accuracy of conversion of the received spectral information into concentration of said analyte in said fluid.

While the invention is susceptible to various modifications and alternative forms, specific embodiments are shown by way of example in the drawings and described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. A system for determining the concentration of an analyte in body fluid, the system comprising:
  an infrared light source delivering substantially monochromatic light sequentially across a predetermined wavelength range;
  a body tissue interface adapted to contact body tissue and to deliver light from said infrared light source to the contacted body tissue;
  a detector adapted to receive spectral information corresponding to infrared light transmitted through the contacted body tissue and to convert the received spectral information into an electrical signal indicative of the received spectral information; and
  a central processing unit adapted to compare the electrical signal to an algorithm built upon correlation with the analyte in the body fluid, the algorithm adapted to convert the received spectral information into the concentration of the analyte in the body fluid, said central processing unit controlling said infrared light source and varying the intensity and timing of the delivery of said monochromatic light within the predetermined wavelength range to improve the accuracy of conversion of the received spectral information into concentration of said analyte in said body fluid.

2. The system of claim 1, wherein said infrared light source is an acoustic optical tunable filter (AOTF) spectrometer.

3. The system of claim 1, wherein said wavelength range is from about 1400 nanometers to about 2500 nanometers.

4. The system of claim 1, wherein said body fluid is extracellular fluid and said analyte is glucose.

5. The system of claim 1, wherein said varying the intensity and timing of the delivery of said monochromatic light comprises modulating said infrared light source to correspond to a spaectrum obtained by interaction of the infrared light with a glucose sample.

6. The system of claim 1, wherein the intensity of said monochromatic light is uniform over said predetermined wavelength range.

7. The system of claim 1, wherein the intensity of said monochromatic light is varied across said predetermined wavelength range to provide spectral information received from said sample having uniform intensity across said predetermined wavelength range.

8. The system of claim 1, wherein said monochromatic light is delivered to said sample for predetermined periods of time at predetermined wavelengths.

9. The system of claim 8, wherein said monochromatic light is delivered to said sample at predetermined wavelengths where the signal-to-noise ratio is the greatest.

10. The system of claim 1 wherein the body tissue interface comprises a clamping device having two plates for contacting the body tissue.

11. The system of claim 10 wherein at least one of the two plates includes a temperature control element for controlling the temperature of the body tissue contacted by the clamping device.

12. The system of claim 1 wherein the wavelength ranges between 750 nanometers and 2500 nanometers.

13. A method for determining the concentration of an analyte in body fluid, the method comprising the acts of:
- delivering substantially monochromatic light from an infrared light source sequentially across a predetermined wavelength range;
- contacting body tissue with a body tissue interface;
- delivering light from said infrared light source to the contacted body tissue;
- receiving spectral information corresponding to infrared light transmitted through the contacted body tissue;
- converting the received spectral information into an electrical signal indicative of the received spectral information;
- comparing the electrical signal to an algorithm built upon correlation with the analyte in the body fluid using a central processing unit; and
- converting the received spectral information into the concentration of the analyte in the body fluid using the algorithm, the central processing unit controlling said infrared light source and varying the intensity and timing of the delivery of said monochromatic light within the predetermined wavelength range to improve the accuracy of conversion of the received spectral information into concentration of said analyte in said body fluid.

14. The method of claim 13, wherein said analyte is glucose.

15. The method of claim 13 further including measuring pressure applied to the body tissue being analyzed; measuring temperature of the body tissue and wherein determining the concentration of the analyte in at least one body fluid comprises using the measured pressure and temperature to correct for spectral information.

16. The method of claim 13 further including measuring temperature of the body tissue and wherein determining the concentration of the analyte in at least one body fluid comprises using the measured temperature to correct for spectral information.

17. The method of claim 13 further including measuring pressure applied to the body tissue being analyzed; and wherein determining the concentration of the analyte in at least one body fluid comprises using the measured pressure to correct for spectral information.

18. The method of claim 13, wherein said wavelength range is from about 1400 nanometers to about 2500 nanometers.

19. The method of claim 13 further including compressing the body tissue.

* * * * *